(12) United States Patent
Cobianu

(10) Patent No.: US 8,980,666 B2
(45) Date of Patent: Mar. 17, 2015

(54) METHOD OF FABRICATING SENSORS HAVING FUNCTIONALIZED RESONATING BEAMS

(75) Inventor: Cornel P. Cobianu, Bucharest (RO)

(73) Assignee: Honeywell Romania s.r.l. (RO)

( * ) Notice: Subject to any disclaimer, the term of this patent is extended or adjusted under 35 U.S.C. 154(b) by 523 days.

(21) Appl. No.: 13/308,878

(22) Filed: Dec. 1, 2011

(65) Prior Publication Data

US 2012/0142135 A1    Jun. 7, 2012

(30) Foreign Application Priority Data

Dec. 2, 2010   (EP) .................................. 10193535

(51) Int. Cl.
| | |
|---|---|
| *H01L 21/00* | (2006.01) |
| *G01N 29/02* | (2006.01) |
| *G01N 29/22* | (2006.01) |
| *B81C 1/00* | (2006.01) |
| *B01L 3/00* | (2006.01) |
| *B82Y 40/00* | (2011.01) |

(52) U.S. Cl.
CPC .......... *G01N 29/022* (2013.01); *G01N 29/222* (2013.01); *B81C 1/00214* (2013.01); *B01L 3/502707* (2013.01); *G01N 2291/021* (2013.01); *G01N 2291/0255* (2013.01); *G01N 2291/0256* (2013.01); *G01N 2291/0427* (2013.01); *B81B 2201/0214* (2013.01); *B81B 2203/0118* (2013.01); *B81B 2207/015* (2013.01); *B81C 2201/0185* (2013.01); *B81C 2203/0118* (2013.01); *B81C 2203/0714* (2013.01); *B81C 2203/0735* (2013.01); *B82Y 40/00* (2013.01)

USPC ..................................... 438/49; 257/E21.002

(58) Field of Classification Search
USPC .......................................................... 438/49
See application file for complete search history.

(56) References Cited

U.S. PATENT DOCUMENTS

| | | | |
|---|---|---|---|
| 2004/0146431 A1* | 7/2004 | Scherer et al. ............. | 422/82.05 |
| 2009/0193874 A1 | 8/2009 | Cobianu et al. | |
| 2010/0238454 A1* | 9/2010 | Pruessner et al. ............. | 356/479 |

FOREIGN PATENT DOCUMENTS

WO    WO-00/66266 A1    11/2000

OTHER PUBLICATIONS

"European Application Serial No, 10193535.1, Partial European Search Report mailed Sep. 12, 2011", 9 pgs.
"European Application Serial No. 10193535.1, Response filed Mar. 5, 2012 to Extended Search Report mailed Sep. 12, 2011", 17 pgs.
Campbell, et al., "Piezoelectric-excited miilimeter-sized cantilever (PEMC) sensors detect *Bacillus anthracis* at 300 spores/mL", *Biosensors and Bioclectronics, 21(9)*, (2006), 1684-1692.

* cited by examiner

*Primary Examiner* — Alexander Ghyka
(74) *Attorney, Agent, or Firm* — Schwegman Lundberg & Woessner, P.A.

(57) ABSTRACT

Some embodiments relate to method of fabricating a sensor. The method includes providing a substrate wafer that includes a suspended beam; adding an adhesive layer to the substrate wafer such that the adhesive layer covers portions of the substrate without covering the suspended beam; positioning a cover wafer onto the adhesive layer such that the suspend beam is exposed to ambient air through openings in the cover wafer; and functionalizing the suspended beam by contacting the suspended beam with materials through the opening in the cover wafer.

10 Claims, 7 Drawing Sheets

METHOD OF FABRICATING SENSORS HAVING FUNCTIONALIZED RESONATING BEAMS

PRIORITY CLAIM AND RELATED APPLICATION

This application claims the benefit of priority under 35 U.S.C. Section 119 to European Patent Application Serial No. 10193535.1, filed Dec. 2, 2010, which application is incorporated herein by reference in its entirety.

BACKGROUND

The global efforts on preserving the health of the planet are focused in some key area like global warming and environmental air quality. One aspect of improving environmental air quality relates to technologies where the gases (e.g., carbon dioxide) that are released from manufacturing processes are captured and sequestered.

Capturing and sequestering gases may in the near future involve tightly controlled processes that include continuous real-time monitoring of emissions. The processes and monitoring that are typically associated with capturing and sequestering gases often require high cost-high power sensors.

One potential technology that may be utilized to produce low-cost and low-power sensors involves integrated resonant sensing technology. This integrated sensing technology is based on vibrating beams that are functionalized for chemisorptive carbon dioxide capture. The beams are typically doubly clamp (nano)beams, cantilever (nano)beams or even nanowires. The beams change their resonance frequency proportional to the amount of gas adsorbed on the beam.

These functionalized resonant sensing beams are typically located on the same chip with an integrated circuit for processing signals from the carbon dioxide sensor. A typical single silicon wafer having diameter of 400 mm may contain hundreds of thousands of on-chip carbon dioxide Nano-Electro-Mechano Sensors and Integrated Circuits (NEMSIC) that communicate with the readout integrated circuit.

One of the drawbacks with existing resonant NEMSIC gas sensing systems may relates to an inability to mass produce such systems. One of the difficulties that is associated with mass producing such systems is the low thermal tolerance of the functionalized resonating beams that are typically a primary component in these types of sensors. The low thermal tolerance is due to the fact that the functionalized resonating beams are usually made of organic materials whose chemical stability deteriorates at temperatures higher than 60-70° C. Since many manufacturing methods require temperate above 60-70° C., it becomes difficult to mass produce sensors that include functionalized resonating beams.

There is a need for a method of fabricating sensors that include functionalized resonating beams which allows (i) preparation of sensing layers in functionalized resonating beams; (ii) cost effective high volume packaging of the sensors, (iii) compatibility with the thermal limits tolerated by the organic material that is used in functionalized resonating beams; and (iv) the sensing surface to have access to the ambient air in order detect a reversible reaction between a particular gas in the ambient air and the functionalized resonating beams.

DETAILED DESCRIPTION

In the following description, reference is made to the accompanying drawings that form a part hereof, and in which is shown by way of illustration specific embodiments which may be practiced. These embodiments are described in sufficient detail to enable those skilled in the art to practice the invention, and it is to be understood that other embodiments may be utilized and that structural, electrical, and optical changes may be made without departing from the scope of the present invention. The following description of example embodiments is, therefore, not to be taken in a limited sense, and the scope of the present invention is defined by the appended claims.

Figure 1:
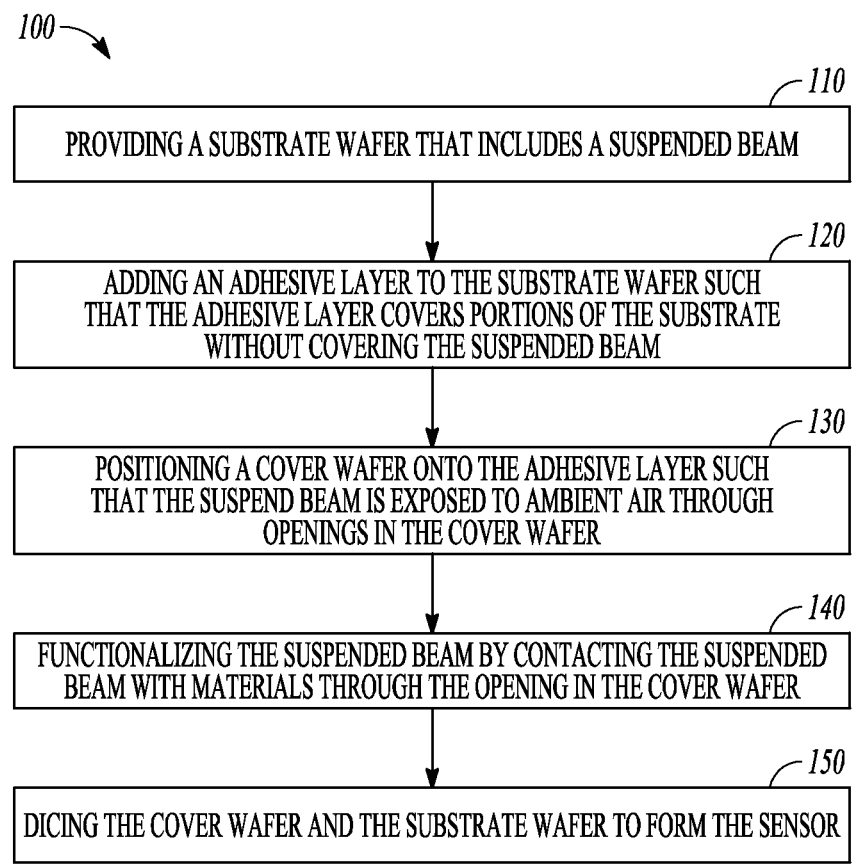
FIG. 1 is a flow diagram illustrating an example method fabricating a sensor.
Figure 2:
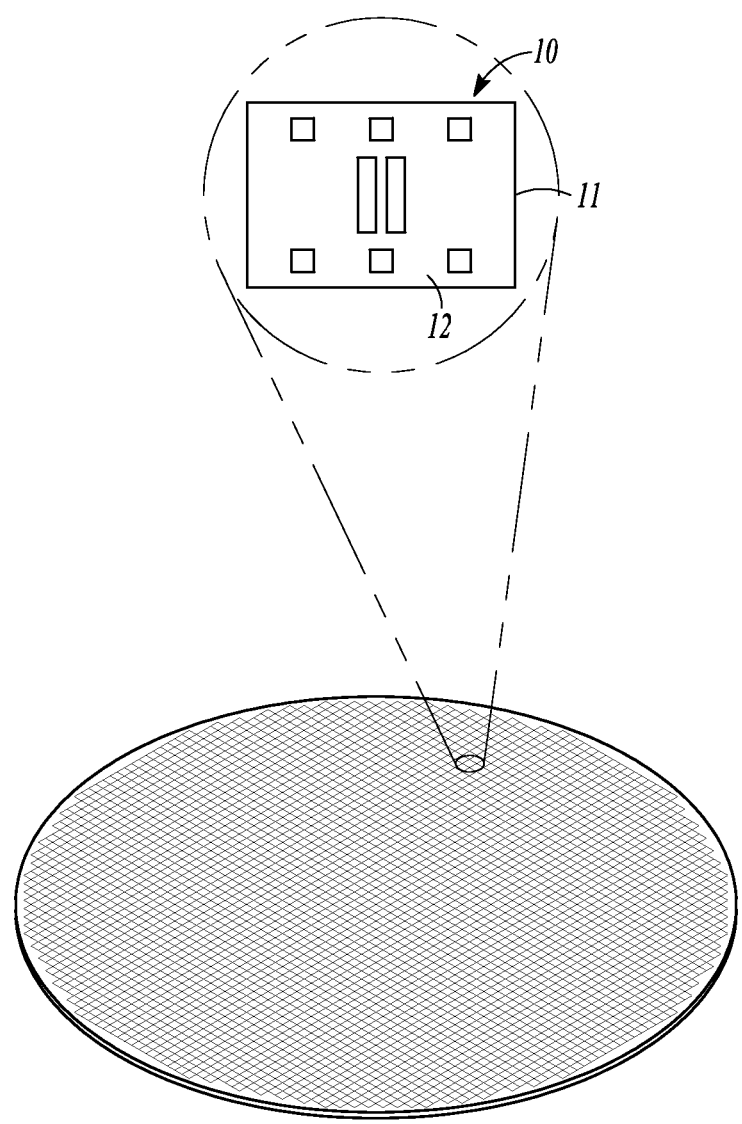
FIG. 2 illustrates an example substrate wafer that includes multiple chips where each chip has at least one suspended beam and the figure includes an enlarged portion that illustrates one example chip.

FIG. 1 illustrates an example method [100] of fabricating a sensor 10. The method includes [110] providing a substrate wafer 12 that includes at least one suspended beam 14 (e.g., a substrate wafer 12 that includes CMOS circuitry or SOI-CMOS circuitry). An example substrate wafer 12 is shown in FIG. 2 with one chip on the substrate wafer 12 enlarged for purpose of clarity.

Figure 3:
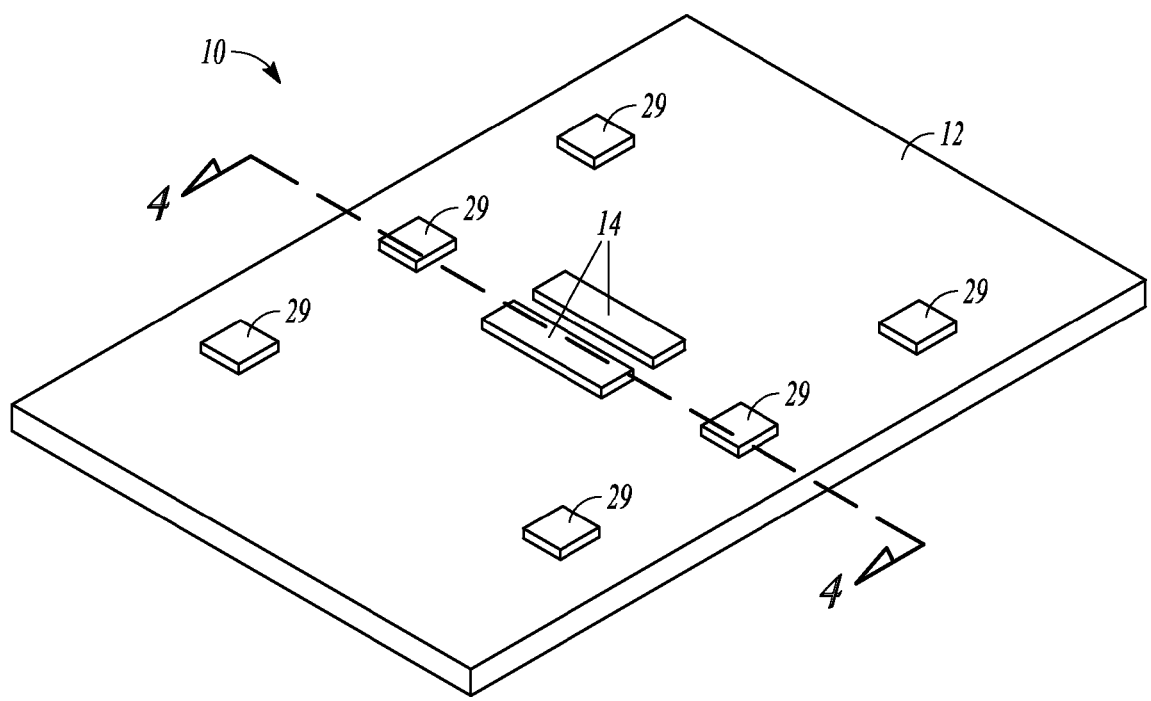
FIG. 3 illustrates an example chip that includes at least one suspended beam.
Figure 4:
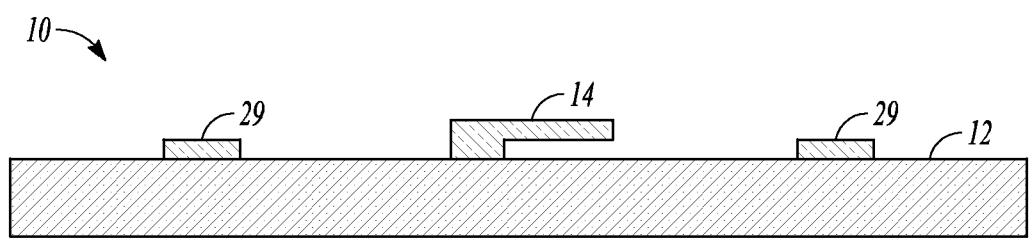
FIG. 4 is a section view of the chip shown in FIG. 3 taken along line 3-3.
Figure 5:
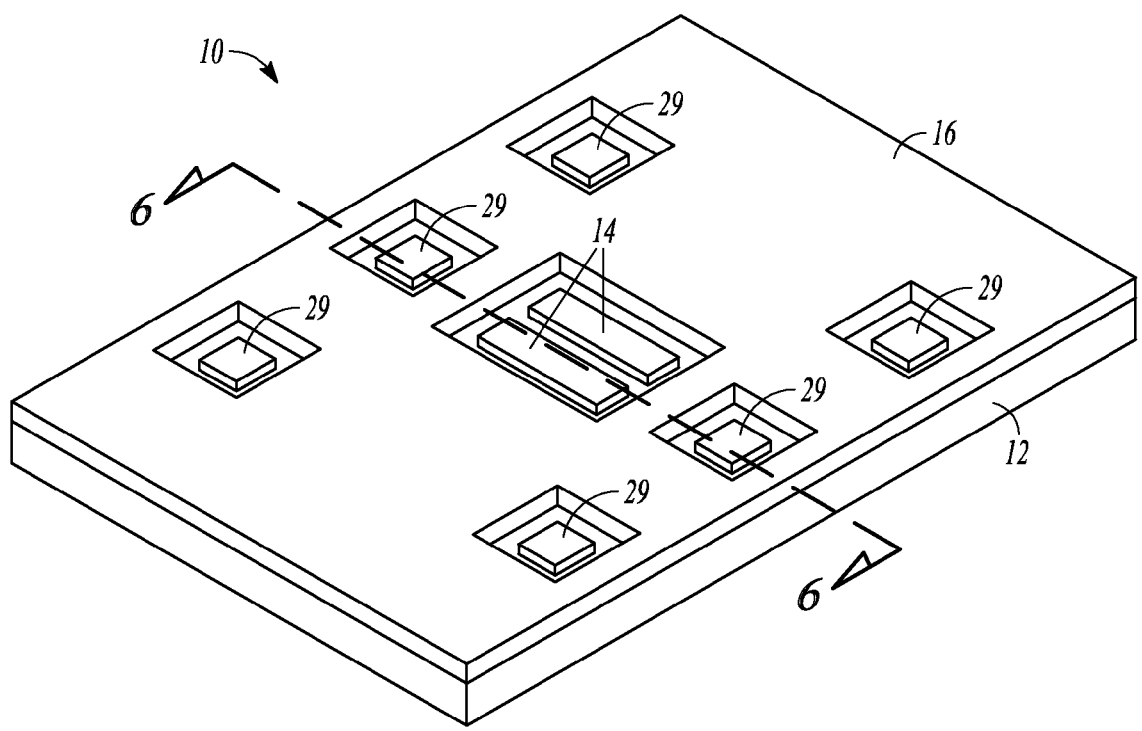
FIG. 5 illustrates the example chip shown in FIG. 3 where the chip is covered with an adhesive layer.
Figure 6:
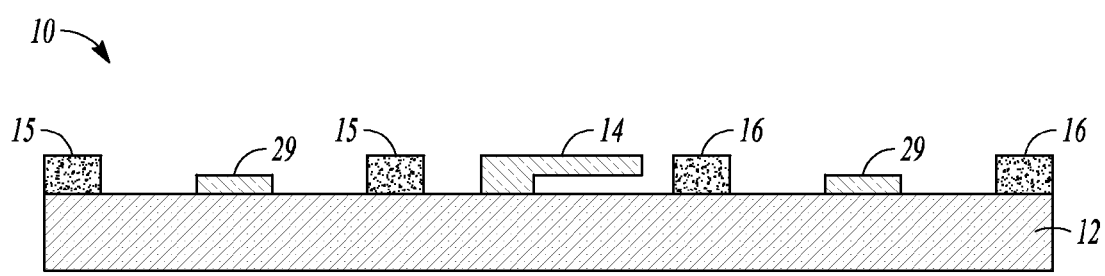
FIG. 6 is a section view of the chip shown in FIG. 5 taken along line 6-6.
Figure 7:
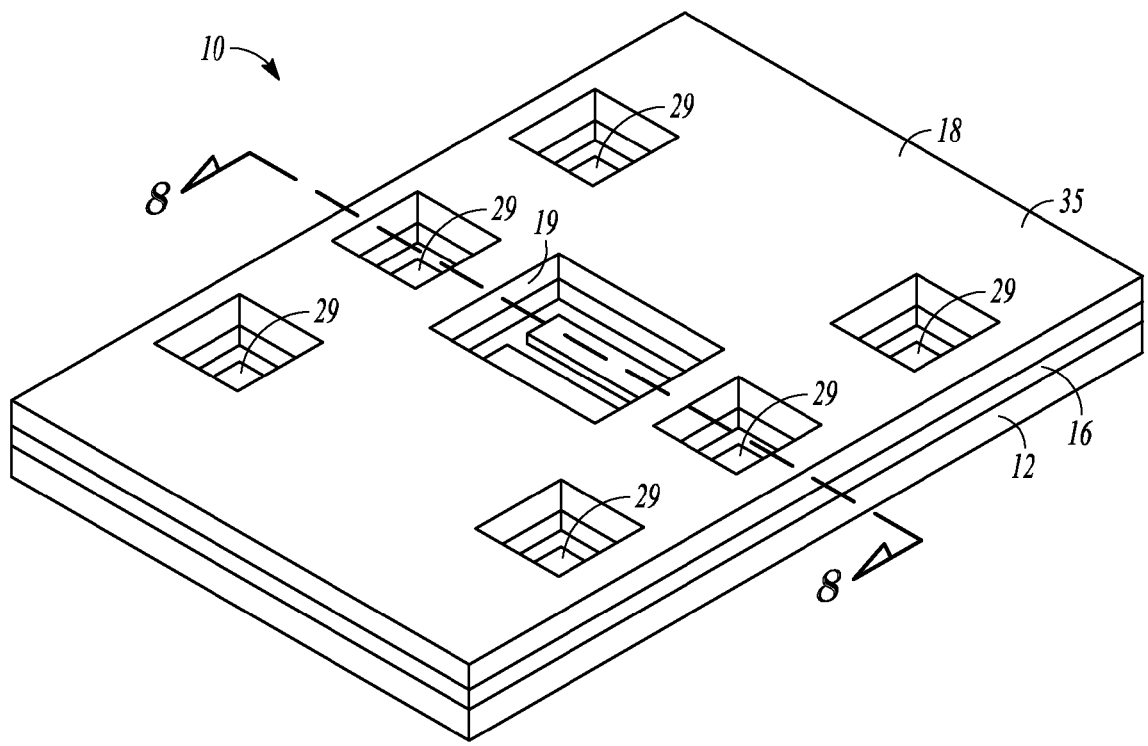
FIG. 7 illustrates the example chip shown in FIG. 3 where a cover has been placed onto the adhesive layer.
Figure 8:
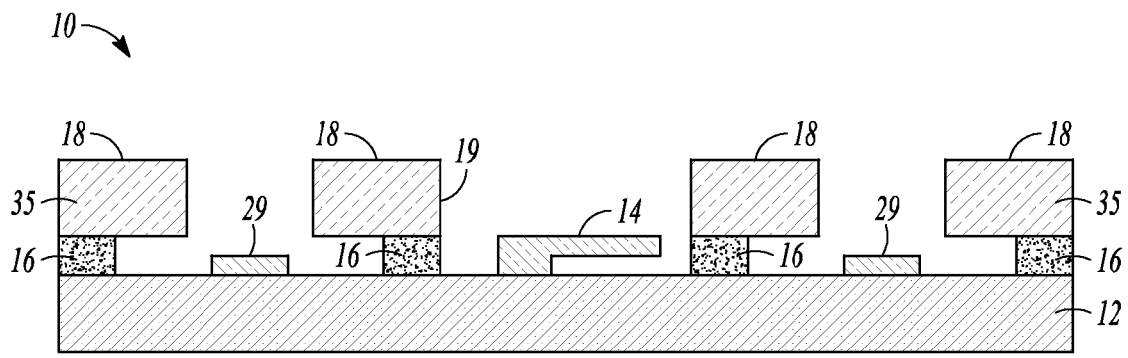
FIG. 8 is a section view of the chip shown in FIG. 7 taken along line 7-7.

FIGS. 3-10 also illustrate one chip only for purposes of clarity even though many of steps described herein refer to wafer level processing. It should be noted that even though FIGS. 3 and 4 show the substrate wafer 12 as having two suspended beams 14, the substrate wafer 12 may include any number of suspended beams 14.

Referring again to FIG. 1, the method [100] further includes [120] adding an adhesive layer 16 to the substrate wafer 12 such that the adhesive layer 16 covers portions of the substrate wafer 12 without covering the suspended beams 14. As an example, the adhesive layer 16 may be added by patterned adhesive polymer bonding. As shown most clearly in FIGS. 5 and 6, the suspended beams 14 are exposed through openings 17 in the adhesive layer 16 for subsequent processing.

In some embodiments, [120] adding an adhesive layer 16 to the substrate wafer 14 such that the adhesive layer 16 covers portions of the substrate wafer 12 without covering the suspended beams 14 includes curing the adhesive layer before functionalizing the suspended beams 14. The adhesive layer 16 may be deposited on the substrate wafer 12 by direct printing or photolithographic methods.

The adhesive layer 16 may be a thermosetting or thermoplastic polymer layer. Some example thermosetting polymers include benzene-cyclo-butene (BCB) and other materials (e.g., liquid crystal polymer or polyimides).

The adhesive layer 16 is preferably a CMOS compatible, low cost, high bond strength polymer adhesive which is thermally curable polymer that becomes mechanically and chemically strong after a thermally activated cross linking polymerization process. As an example, the adhesive layer 16 may have a thickness in the range of 1.5-3 micrometers.

When the adhesive layer 16 is formed of BCB, the adhesive layer 16 may be pre-cured in an oxygen free ambient environment at temperatures between 190 and 200° C. for 30 minutes in order to reach a partial polymerization level of about 30-50%. During this stage the solvents and volatile components are removed from the BCB in order to avoid something similar happening during curing. The pre-curing also helps the BCB deform and wet the surface of the substrate wafer 12.

An adhesion promoter may be applied to the substrate wafer 12 in regions where the adhesive layer 16 are to be applied in order to facilitate bonding with the substrate wafer 12. The adhesive promoter may be applied by mask less direct printing methods.

In the illustrated example embodiments, the bond pad areas and sensing and reference beams area are not covered with adhesive layer 16. All the rest of the chip is covered with the adhesive layer 16 to promote bonding stability and heat transfer outside of the silicon chip.

Referring again to FIG. 1, the method [100] further includes [130] positioning a cover wafer 18 onto the adhesive layer 16 such that the suspend beams 14 are exposed to ambient air through openings 19 in the cover wafer 18. As shown most clearly in FIGS. 7 and 8, the suspend beams 14 are exposed to ambient air through openings 19 in the cover wafer 18.

In some embodiments, [130] positioning a cover wafer 18 onto the adhesive layer 16 such that the suspend beams 14 are exposed to ambient air through openings 19 in the cover wafer 18 includes fabricating the openings 19 in the cover wafer 18. As an example, the cover wafer 18 may be formed of silicon such that fabricating the openings 19 in the cover wafer 18 includes anistropic etching of the cover wafer 18.

The openings 19 in the cover wafer 18 in the cover wafer (which create access zones to the suspended beams 14 and possibly bond pads) by a selective masking and deep etching process. As an example, KOH etching or deep reactive ion etching (DRIE) may be used for silicon cover wafer. As another example, DRIE or sand blasting may be used for a glass cover wafer.

In some embodiments, [130] positioning a cover wafer 18 onto the adhesive layer 16 such that the suspend beams 14 are exposed to ambient air through openings 19 in the cover wafer 18 includes bringing the substrate wafer 12 (which includes the adhesive layer 16) and the cover wafer 18 to a bonding tool where they are placed on a bonding fixture. The bonding fixture is then transferred to a bonding chamber that initially has a vacuum level of 10-3 mbar. The binding tool applies a bonding pressure of about 0.4 MPa while the wafer stack is heated to about 250° C. for 30-560 minutes to perform the curing process for final BCB based adhesive wafer bonding.

Figure 9:
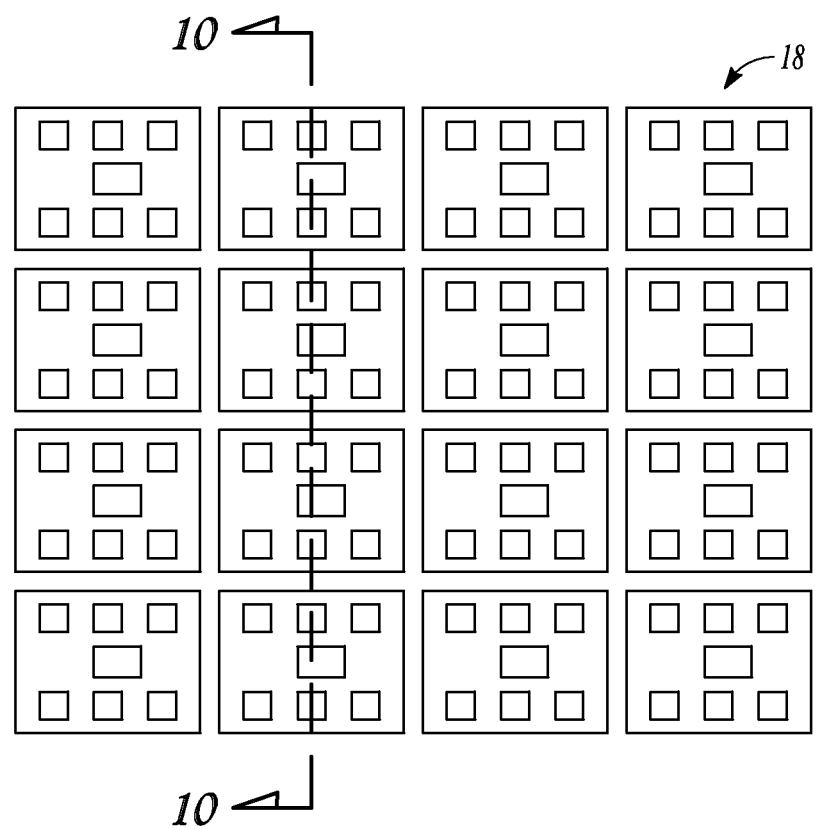
FIG. 9 illustrates a portion of the cover wafer that is used in the chip shown in FIGS. 7 and 8.
Figure 10:
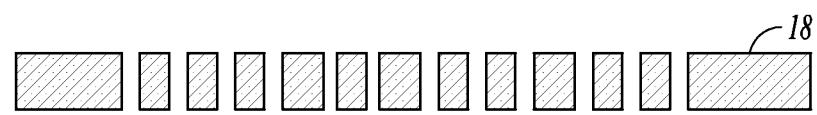
FIG. 10 is a section view of the portion of the cover wafer shown in FIG. 9 taken along line 10-10.

Referring again to FIG. 1, the method [100] further includes [140] functionalizing the suspended beams 14 by contacting the suspended beams 14 with materials through the openings 19 in the cover wafer 18. FIGS. 9 and 10 illustrate an example cover wafer 18 that may be used in the method [100].

In some embodiments, [140] functionalizing the suspended beams 14 by contacting the suspended beams 14 with materials through the openings 19 may include direct printing of the materials through the openings 19 in the cover wafer 18. As an example, direct printing of the materials may be done with high positioning accuracy by means of dip pen nanolithography (DPN) tools.

Functionalizing the suspended beams 14 after the cover wafer 18 has been bonded to the adhesive layer 16 prevents having the functionalized surface of the functionalized suspended beams 14 exposed to undesirably high temperatures that are used during the bonding process.

As used herein, a "functionalized beam" means a beam that is capable of absorbing and/or reacting with a particular gas. It should be noted that a functionalized beam may include functionalized surfaces that are formed as part of a layer or coating that is added to the suspended beams 14.

In some embodiments, [140] functionalizing the suspended beam by contacting the suspended beams 14 with materials through the openings 19 in the cover wafer 18 includes drying the deposited material. As an example, drying the deposited material may include changing the material from a liquid to a solid.

The technology associated with functionalizing the suspended beams 14 will depend in part on the type of gas that is to be detected by the sensor 10. As discussed above, only the regions of the chip where the suspended beams 14 are located is exposed for the whole sequence of chemical processes that are needed for functionalization. All the other parts of the chip are protected by the substrate wafer 12, adhesive layer 16 and the cover wafer 18, which are chemically resistant to processes used for functionalization (e.g., silicon functionalization).

As shown in FIG. 1, the method [100] may further include [150] dicing the cover wafer 18 and the substrate wafer 12 to form the sensor 10. It should be noted the cover wafer 18 and the substrate wafer 12 may be diced by any known method.

Figure 11:
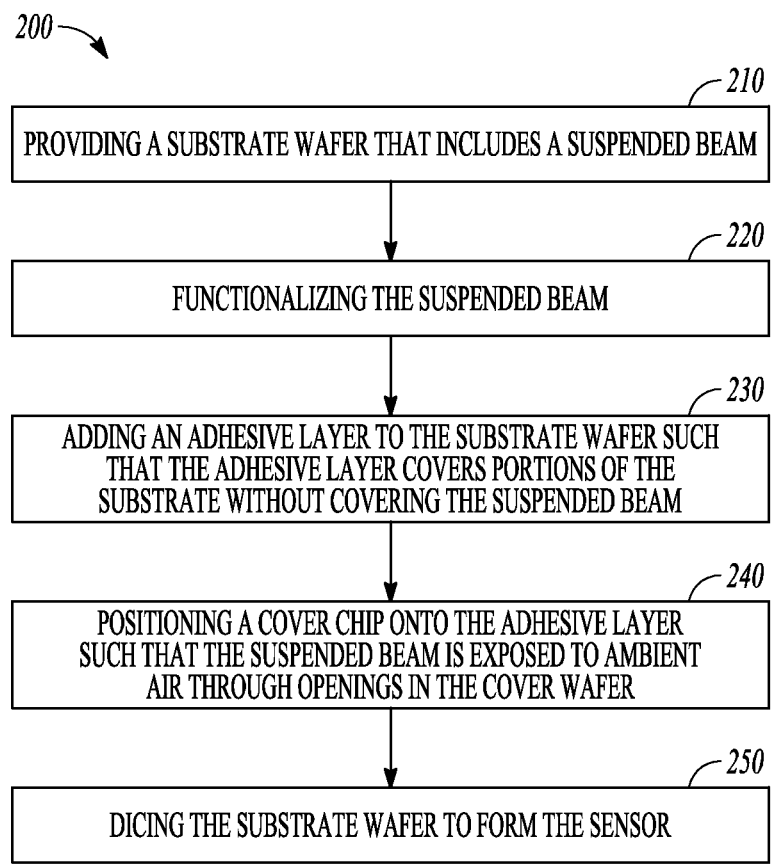
FIG. 11 is a flow diagram illustrating another example method fabricating a sensor.

FIG. 11 illustrates an example method [200] of fabricating a sensor 10. The method includes [210] providing a substrate wafer 12 that includes at least one suspended beam 14 (e.g., a substrate wafer 12 that includes CMOS circuitry or SOI-CMOS circuitry).

The method [200] further includes [220] functionalizing the suspended beam and [230] adding an adhesive layer 16 to the substrate wafer 12 such that the adhesive layer 16 covers portions of the substrate wafer 12 without covering the functionalized suspended beams 14. As shown most clearly in FIGS. 5 and 6, the suspended beams 14 are exposed through openings in the adhesive layer 16 for subsequent processing.

In some embodiments, [220] functionalizing the suspended beams 14 includes direct printing of the materials onto the suspended beams. As an example, direct printing of the materials may be done with high positioning accuracy by means of dip pen nanolithography (DPN) tools.

In some embodiments, [220] functionalizing the suspended beams includes drying the deposited material. As an example, drying the deposited material may include changing the material from a liquid to a solid. The technology associated with functionalizing the suspended beams 14 will depend in part on the type of gas that is to be detected by the sensor 10.

Referring again to FIG. 11, the method [200] further includes [240] positioning a cover chip 18 onto the adhesive layer 16 such that the suspended beams 14 are exposed to ambient air through openings 19 in the cover chip 18.

In some embodiments, [240] positioning a cover chip 18 onto the adhesive layer 16 such that the suspended beams 14 are exposed to ambient air through openings 19 in the cover chip 18 includes fabricating openings 19 in a cover wafer (see, e.g., FIG. 9) and dicing the cover wafer to form the cover chip 18.

Positioning a cover chip 18 onto the adhesive layer 16 allows only known good glass dies to be bonded to known good dies on the substrate wafer 12. As an example, only good cover chips 18 may be picked and placed process on the silicon sensor chips. Appropriate pick and place procedures may serve to facilitate proper alignment before bonding good cover chips 18 to respective silicon sensor chips.

In some embodiments, the adhesive layer 16 may be cured by using ultraviolet light (UV) at room temperature in order to preserve chemical properties of functionalized suspended beams 14. When a UV curable adhesive is used as part of the adhesive layer 16, the chip 18 may be made of glass so that the chip 18 is transparent to UV.

One example UV curable adhesive may be a thermosetting polymer, such as NEA 121 UV adhesive from Norland product or SU8 epoxy)\. In some embodiments, adhesive curing may take place in UV for 10 minutes where the UV is provided by a UV lamp that illuminates at 14 mW/cm2. One example lamp is model no. SB-100P manufactured by Spectronics).

As shown in FIG. 11, the method [200] may further include [250] dicing the substrate wafer 12 to form the sensor 10. It should be noted the cover the substrate wafer 12 may be diced by any known method.

In the method [200] described herein, the suspended beams 14 are functionalized before the cover chip 18 is bonded to the adhesive layer 16. The method allows for easier separation of known good chips from the rest of the chips that are on substrate wafer 12 after wafer level testing is done on the substrate wafer 12.

Since the suspended beams 14 are functionalized before the cover chip 18 is placed on the adhesive layer 16, the packaging process needs to preserve the quality of the functionalized (i.e., organic) layer. Therefore, the cover chip 18 should be bonded to the substrate wafer 12 at room temperature.

The Abstract is provided to comply with 37 C.F.R. §1.72(b) to allow the reader to quickly ascertain the nature and gist of the technical disclosure. The Abstract is submitted with the understanding that it will not be used to interpret or limit the scope or meaning of the claims.

The invention claimed is:

1. A method of fabricating a sensor comprising:
providing a substrate wafer that includes a suspended beam;
adding an adhesive layer to the substrate wafer such that the adhesive layer covers portions of the substrate without covering the suspended beam;
positioning a cover wafer onto the adhesive layer such that the suspend beam is exposed to ambient air through openings in the cover wafer; and
functionalizing the suspended beam by contacting the suspended beam with materials through the opening in the cover wafer.

2. The method of claim 1, wherein contacting the suspended beam with materials through the opening in the cover wafer includes direct printing of the materials through the opening in the cover wafer.

3. The method of claim 2, wherein direct printing of the materials through the opening in the cover wafer includes direct printing the material using dip pen nanolithography.

4. The method of claim 1, wherein functionalizing the suspended beam by contacting the suspended beam with materials through the opening in the cover wafer includes drying the deposited material.

5. The method of claim 4, wherein drying the deposited material includes changing the material from a liquid to a solid.

6. The method of claim 1, further comprising dicing the cover wafer and the substrate wafer to form the sensor.

7. The method of claim 1, wherein adding an adhesive layer to the substrate wafer such that the adhesive layer covers portions of the substrate without covering the suspended beam includes curing the adhesive layer before functionalizing the suspended beam.

8. The method of claim 1, wherein positioning a cover wafer onto the adhesive layer such that the suspend beam is exposed to ambient air through openings in the cover wafer includes fabricating the openings in the cover wafer.

9. The method of claim 8, wherein the cover wafer is formed of silicon such that fabricating the openings in the cover wafer includes anistropic etching of the cover wafer.

10. The method of claim 1 wherein providing a substrate wafer that includes a suspended beam includes providing a substrate wafer that includes CMOS circuitry.

* * * * *